US007923227B2

(12) United States Patent
Hickey et al.

(10) Patent No.: US 7,923,227 B2
(45) Date of Patent: Apr. 12, 2011

(54) METHOD OF CONVERSION OF SYNGAS USING MICROORGANISM ON HYDROPHILIC MEMBRANE

(75) Inventors: Robert Hickey, Okemos, MI (US); Rahul Basu, Naperville, IL (US); Rathin Datta, Chicago, IL (US); Shih-Perng Tsai, Naperville, IL (US)

(73) Assignee: Coskata, Inc., Warrenville, IL (US)

( * ) Notice: Subject to any disclaimer, the term of this patent is extended or adjusted under 35 U.S.C. 154(b) by 0 days.

(21) Appl. No.: 12/574,499

(22) Filed: Oct. 6, 2009

(65) Prior Publication Data

US 2010/0047886 A1    Feb. 25, 2010

Related U.S. Application Data

(63) Continuation-in-part of application No. 11/972,454, filed on Jan. 10, 2008, which is a continuation-in-part of application No. 11/781,717, filed on Jul. 23, 2007, application No. 12/574,499, which is a continuation-in-part of application No. 12/036,007, filed on Feb. 22, 2008.

(60) Provisional application No. 60/942,938, filed on Jun. 8, 2007.

(51) Int. Cl.
*C12P 7/06* (2006.01)

(52) U.S. Cl. ......... 435/161; 435/41; 435/136; 435/157; 435/297.1; 435/297.2; 435/297.3; 435/297.4

(58) Field of Classification Search ................... 435/41, 435/136, 157, 161, 297.1–297.4
See application file for complete search history.

(56) References Cited

U.S. PATENT DOCUMENTS

| | | | | |
|---|---|---|---|---|
| 4,442,206 A | * | 4/1984 | Michaels et al. | 435/71.1 |
| 6,844,187 B1 | * | 1/2005 | Wechsler et al. | 435/297.2 |
| 2003/0211585 A1 | * | 11/2003 | Gaddy et al. | 435/161 |
| 2005/0260739 A1 | * | 11/2005 | Rosen et al. | 435/254.21 |
| 2006/0096912 A1 | * | 5/2006 | Nussbaumer et al. | 210/500.29 |
| 2006/0163157 A1 | * | 7/2006 | Cote et al. | 210/615 |

OTHER PUBLICATIONS

Inloes et al. Ethanol production by *Saccharomyces cerevisiae* immobilized in hollow-fiber membrane bioreactors. Applied and Environmental Microbiology. p. 267-278. Jul. 1983.*

* cited by examiner

*Primary Examiner* — Michael A Marcheschi
*Assistant Examiner* — Jameson Q Ma (57) ABSTRACT

A stable system for producing liquid products such as ethanol, butanol and other chemicals from syngas components contacts CO or a mixture of $CO_2$ and $H_2$ with a hydrophilic membrane under anaerobic conditions and transfers these components into contact with microorganisms contained as a biofilm on the membrane. Maintaining the microorganisms as a biolayer on the surface of the membrane facilitates cleaning of the membrane surface that retains the biofilm. In addition the shell gas space that surrounds the membranes may be flooded to reduce or remove the biofilm. Agitation of the liquid, by for example the bubbling of gas in the surrounding shell space, can fully or partially remove the biofilm from the membrane.

20 Claims, 7 Drawing Sheets

METHOD OF CONVERSION OF SYNGAS USING MICROORGANISM ON HYDROPHILIC MEMBRANE

CROSS REFERENCE TO RELATED APPLICATIONS

This application is a continuation in part of U.S. application Ser. No. 11/972,454 filed Jan. 10, 2008 which is a continuation in part of U.S. application Ser. No. 11/781,717 filed Jul. 23, 2007 which is an application claiming benefit under 35 USC 119(c) of U.S. Provisional Patent Application Ser. No. 60/942,938 filed Jun. 8, 2007 and a continuation in part of U.S. application Ser. No. 12/036,007 filed Feb. 22, 2008.

FIELD OF THE INVENTION

This invention relates to the biological conversion of CO and mixtures of $CO_2$ and $H_2$ to liquid products.

DETAILED DESCRIPTION

Background

Biofuels production for use as liquid motor fuels or for blending with conventional gasoline or diesel motor fuels is increasing worldwide. Such biofuels include, for example, ethanol and n-butanol. One of the major drivers for biofuels is their derivation from renewable resources by fermentation and bioprocess technology. Conventionally, biofuels are made from readily fermentable carbohydrates such as sugars and starches. For example, the two primary agricultural crops that are used for conventional bioethanol production are sugarcane (Brazil and other tropical countries) and corn or maize (U.S. and other temperate countries). The availability of agricultural feedstocks that provide readily fermentable carbohydrates is limited because of competition with food and feed production, arable land usage, water availability, and other factors. Consequently, lignocellulosic feedstocks such as forest residues, trees from plantations, straws, grasses and other agricultural residues may become viable feedstocks for biofuel production. However, the very heterogeneous nature of lignocellulosic materials that enables them to provide the mechanical support structure of the plants and trees makes them inherently recalcitrant to bioconversion. Also, these materials predominantly contain three separate classes of components as building blocks: cellulose (C6 sugar polymers), hemicellulose (various C5 and C6 sugar polymers), and lignin (aromatic and ether linked hetero polymers).

For example, breaking down these recalcitrant structures to provide fermentable sugars for bioconversion to ethanol typically requires pretreatment steps together with chemical/enzymatic hydrolysis. Furthermore, conventional yeasts are unable to ferment the C5 sugars to ethanol and lignin components are completely unfermentable by such organisms. Often lignin accounts for 25 to 30% of the mass content and 35 to 45% of the chemical energy content of lignocellulosic biomass. For all of these reasons, processes based on a pretreatment/hydrolysis/fermentation path for conversion of lignocellulose biomass to ethanol, for example, are inherently difficult and often uneconomical multi-step and multi conversion processes.

An alternative technology path is to convert lignocellulosic biomass to syngas (also known as synthesis gas, primarily a mix of CO, H2 and CO2 with other components such as CH4, N2, NH3, H2S and other trace gases) and then ferment this gas with anaerobic microorganisms to produce biofuels such as ethanol, n-butanol or chemicals such as acetic acid, butyric acid and the like. This path can be inherently more efficient than the pretreatment/hydrolysis/fermentation path because the gasification step can convert all of the components to syngas with good efficiency (e.g., greater than 75%), and some strains of anaerobic microorganisms can convert syngas to ethanol, n-butanol or other chemicals with high (e.g., greater than 90% of theoretical) efficiency. Moreover, syngas can be made from many other carbonaceous feedstocks such as natural gas, reformed gas, peat, petroleum coke, coal, solid waste and land fill gas, making this a more universal technology path.

However, this technology path requires that the syngas components CO and H2 be efficiently and economically dissolved in the aqueous medium and transferred to anaerobic microorganisms that convert them to the desired products. And very large quantities of these gases are required. For example, the theoretical equations for CO or H2 to ethanol are:

6CO+3H2O→C2H5OH+4CO2

6H2+2CO2→C2H5OH+3H2O

Thus 6 moles of relatively insoluble gases such as CO or H2 have to transfer to an aqueous medium for each mole of ethanol. Other products such as acetic acid and n-butanol have similar large stoichiometric requirements for the gases.

Furthermore, the anaerobic microorganisms that bring about these bioconversions generate very little metabolic energy from these bioconversions. Consequently they grow very slowly and often continue the conversions during the non-growth phase of their life cycle to gain metabolic energy for their maintenance. To get high yields and production rates the cell concentrations in the bioreactor need to be high and this requires some form of cell recycle or retention.

Cell retention by formation of biofilms is a very good and often inexpensive way to increase the density of microorganisms in bioreactors. This requires a solid matrix with large surface area for the microorganisms to colonize and form a biofilm that contains the metabolizing microorganisms in a matrix of biopolymers that the microorganisms generate. Trickle bed and some fluidized bed bioreactors make use of biofilms to retain microorganisms on solid surfaces while providing dissolved gases in the liquid by flow past the solid matrix. They suffer from either being very large or unable to provide sufficient gas dissolution rates.

Particular forms of membranes have found use in supporting specific types of microorganisms for waste water treatment processes. U.S. Pat. No. 4,181,604 discloses the use of hollow fiber membranes for waste treatment where the outer surface of the fibers supports a layer of microorganisms for aerobic digestion of sludge.

U.S. Ser. No. 11/781,717 filed Jul. 23, 2007, U.S. Ser. No. 11/833,864 filed Aug. 3, 2007 and U.S. Ser. No. 11/972,454 filed Jan. 10, 2008 disclose a membrane based bioreactor wherein anaerobic bacteria that have the ability to convert syngas to ethanol or other liquids have formed biofilms on the outer surface of hydrophobic membranes with the syngas fed to the bacterial biofilm through the inner surface of the membrane. Such a bioreactor system has been able to directly convert the primary components of synthesis gas, CO and H2/CO2, to ethanol and other liquid products such as n-butanol, acetic acid and butyric acid. In these systems the gas flows through a porous region of a hydrophobic membrane and then reaches a biofilm which is hydrophilic. One drawback of this arrangement is that if water reaches and deposits/condenses on the hydrophobic porous region it will severely decrease the gas transfer rate.

U.S. Ser. No. 12/036,007 filed Feb. 22, 2008 discloses an asymmetric membrane based bioreactor wherein anaerobic bacteria that have the ability to convert syngas to ethanol or other liquids have formed biopores to the retain biofilms therein on the outer, spongy, surface of the membrane to feed the syngas directly to the bacterial biofilm and not through membrane. The lumen of the membrane transports fermentation liquid or broth past the membrane for feeding of nutrients to the biofilm and reflux of liquid products from the biofilm back through the membrane and into the fermentation liquid. Asymmetric membranes are known for use in a variety of membrane separations processes such as ultra and nano filtration. Asymmetric membranes are typically hydrophilic and have a relatively tight semi permeable "skin" layer on one side supported on a porous "spongy" polymer layer. U.S. Pat. Nos. 4,442,206 and 4,440,853 show the use of the "spongy" polymer layer in an asymmetric membrane to immobilize microorganisms for certain biological processes that use soluble carbon sources. However, the spongy layer of the asymmetric membrane may cause the biofilm to adhere too tightly to the membrane and prevent suitable cleaning of the membrane pores when needed. In certain cases this can result in excessive downtime and loss of production capacity. The build-up of biological products and cell debris within the pores can limit the run time between necessary cleanings in the Biopore approach.

SUMMARY OF THE INVENTION

This invention is a process for using anaerobic microorganisms in the form of a biofilm to convert syngas (herein defined to include any gas containing CO and/or a mixture of $CO_2$ and $H_2$ as its principal components) in an improved retaining arrangement to provide a stable system for enhancing the production of liquid products such as ethanol, butanol, hexanol, and other chemicals from a syngas stream while facilitating maintenance of the biofilm and periodic scouring of the biofilm. A hydrophilic membrane provides pores that permit the permeation of fermentation liquid and nutrients from the liquid side of a membrane to the gas side while promoting the growth of microorganism colonies on the surface of the gas side of the membrane. Simultaneously, the other side (gas side) of the hydrophilic membrane remains exposed to fermentation liquid that permeates to the biofilm. The invention retains the biofilm on a surface of the membrane that excludes any substantial penetration of the biofilm beyond the support surface and into the membrane.

During syngas fermentation with the bioreactor process of this invention, carbon monoxide or hydrogen/carbon dioxide from the syngas diffuses into the biofilm on the surface of the gas side of the microporous porous membrane wall and is converted by the immobilized microorganisms into ethanol or other water-soluble products, which is then diffused into the aqueous stream flowing over the liquid side of the membrane that gets carried out of the bioreactor. The immobilized microorganisms remain hydrated through contact with the aqueous stream that passes through the hydrophilic membrane.

Therefore, the hydrophilic membrane establishes an interface to provide moisture and trace nutrients that permeate from the liquid side toward the contained microorganisms while simultaneously extracting liquid products formed by the microorganisms. The extracted permeate flows across the membrane into the liquid medium. Thus the desired products and the syngas from which they are produced flow through the membrane in the same direction, from the gas side to the liquid side.

Placement of the membrane layer between the microorganisms and the liquid simplifies the operation of downstream separation facilities. The membrane provides a substantial barrier between the microorganisms and the product containing liquid that keeps the liquid flowing to separation facilities free of microorganisms and other biological contaminants. Preventing virtually all biological contaminants from entering the liquid effluent removes the need for filtering and/or recycling of such materials.

The hydrophilic membrane may be formed from any material or assemblage of materials that provide the necessary occluding of microorganisms from the membrane pores in contact therewith and the desired hydration of the biofilm with fermentation liquid from the opposite side of the membrane. The use of hydrophilic materials enhances performance of the membrane by allowing easy movement of the water through the membrane. In most cases the membrane will comprise a single material but multiple materials and layers may be used.

The membrane may take on a variety of configurations. For example the membrane may comprise hollow fibers or flat sheets whether in flat or spiral wound configurations. Suitable housings may retain the membrane for co-current, counter-current, or cross-flow with respect to the circulation of the liquid on one side of the membrane and the bulk gas flow on the opposite side. In the case of hollow fibers, circulation of the syngas on the outside of the fibers facilitates a horizontal orientation of the fibers so that the bioreactor may work well whether extending in a principally horizontal or vertical direction.

This invention also improves operations for the circulation of liquid on the lumen side of hollow fiber membranes by providing a well defined liquid flow path and providing a contiguous space for gas flow on the outside of the membrane. This permits very high density packing of the membrane elements into membrane assemblies without fear of disrupting liquid flow patterns and creating stagnant areas for the circulating fluid. As a result the bioreactor system of this invention requires an overall smaller working volume than other proposed systems for conversion of syngas by fermentation.

In a variety of different arrangements depicted herein the CO and $H_2/CO_2$ from the syngas are utilized and a gradient for their transport from the gas feed side is created due to biochemical reaction in the biofilm retained on the gas side of the membrane. This reaction creates liquid fuel or chemicals such as ethanol, acetic acid and other products which diffuse into the liquid and are removed via circulation of the liquid that refluxes back across the membrane carrying the liquid products.

Accordingly this invention merges the advantages of both the liquid submerged biofilm and the hydrophilic membrane in the above described membrane bioreactor approaches. In this Membrane Supported Biofilm Reactor [MSBR] configuration the fermentation liquid is fed to one side of a hydrophilic microporous membrane to a biofilm on the surface of the membrane. The syngas is on the opposite side of the membrane so that microorganisms have direct gas phase contact of the syngas with the biofilm. The instant invention typically pumps the fermentation liquid containing nutrients to the side of the membrane opposite the biofilm. The liquid readily diffuses through the membrane to the biofilm that grows on the biofilm side of the membrane surface. Ethanol and other liquid products produced from the syngas by the biofilm readily diffuse back through the membrane into the fermentation liquid for recovery and ultimate separation and purification. Thus the advantages of both the biofilm and biopore type MSBR are obtained and the disadvantages of each mitigated using this hybrid of these two other approaches.

The principal advantage of this approach is that the biofilm is on the surface and not in the membrane pores. As a result control of the biofilm depth and cleaning of the membrane surface is much easier and requires much less time. Filling the gas contact space up with water and sparging this space with gas, such as tail gas from the process or fresh syngas, can be used to control/waste excess biomass. The liquid can be quickly drained and the biomass sent to processing.

By controlling the pressure on the liquid side the depth of the biofilm can be regulated by limiting the water penetration. This can be important in ensuring sufficient dissolved CO penetrates into the entire biofilm to achieve high selectivity for the production of desired products, for example ethanol versus acetate.

One unique feature of the instant invention is seeding or biofilm formation, which is easier in this approach than the other designs. For example when this hybrid system uses hollow fiber membranes (HF), inoculum can be fed into the shell side and the pump that normal feeds flow through the lumen used in the suction mode. This will allow the biomass to be drawn onto the shell side surface as a film immediately. Reversal of the flow from vacuum to slight pressure and hydration of the biofilm is maintained.

In one form this invention is a process for converting a feed gas containing at least one of CO or a mixture of CO2 and H2 to a liquid product under anaerobic conditions and delivering the liquid product to a fermentation liquid. The process passes a feed gas to a biofilm comprising microorganisms that produce liquid products from the feed gas. A biofilm exclusion surface of the gas contacting side of a hydrophilic membrane retains the biofilm inhibits penetration of the biofilm therein. The biofilm exclusion surface may do so in any manner for example by limiting only having pores with effective diameters of no greater than 0.5 μm on its surface or providing sufficient tortuosity that the biofilm cannot grow significantly past the surface. A fermentation liquid comprising water and nutrients passes across a porous surface of a liquid contacting side of the membrane. Fermentation liquid permeates from the liquid contacting side through the membrane and into contact with the biofilm. Fermentation liquid containing liquid products from the biofilm refluxes from the biofilm through the membrane and to the liquid contacting side of the membrane. The process collects fermentation liquid containing liquid products from the liquid contacting side of the membrane to recover liquid products from the process.

In a more specific form of this invention for converting the feed gas the process passes the feed gas to a feed gas chamber having fluid communication with a biofilm retained on a biofilm exclusion surface on the outside of a hydrophilic membrane having a hollow fiber form with a central lumen wherein the biofilm exclusion surface is the outer surface of the hollow fiber membrane and the biofilm exclusion surface inhibit penetration of the biofilm into the membrane by no more than 10 μm into the biofilm exclusion surface. Typically the hollow fiber membrane will have an outer diameter of between 0.4 to 2.8 mm, a lumen with a diameter of 0.3 to 1.2 mm, and a pore size of 0.5 μm or less for inhibiting penetration of the biofilm into the pores. The fermentation liquid comprising water and nutrients flows from a liquid supply chamber through the lumen and across a porous surface of the membrane to permeate fermentation liquid from the lumen through the membrane wall and into contact with the biofilm. The liquid products from the biofilm reflux through the membrane wall and into the lumen for collection in a liquid recovery chamber. The fermentation liquid passes from the liquid recovery chamber to a product recovery section to recover liquid products from the process.

In another specific form the process converts the feed gas to ethanol by passing the feed gas to a feed gas chamber that houses a plurality of hollow fiber membranes. The feed gas chamber communicates the feed gas with a biofilm formed on the membrane comprising microorganisms that produce ethanol from the feed gas. The outer surface of the membrane has a pore size of 0.5 μm or less for inhibiting penetration of the biofilm into the pores of the membrane. The fermentation liquid flows from a liquid supply chamber through the lumens of the membranes and across a porous surface of the membrane to permeate fermentation liquid from the lumen through the membrane wall and into contact with the biofilm. Fermentation liquid containing ethanol passes from the biofilm, through the membrane wall and into the lumen for collection of fermentation liquid containing ethanol in a liquid recovery chamber and recovery of ethanol from the fermentation liquid in a product recovery section. The process maintains the pressure of the liquid in the lumen higher than the pressure in the feed gas chamber and the thickness of the biofilm on the membranes is adjusted by changing the relative pressure between the feed gas chamber and the liquid in the lumen.

In yet another form of this invention the syngas may pass through multiple banks of asymmetric membranes in parallel or serial flow. A particularly useful form of the invention includes the preferential removal of the carbon dioxide (CO2) gas that is formed in the bioconversion process from the syngas as it passes serially through multiple banks of hydrophilic membranes.

DETAILED DESCRIPTION OF THE INVENTION

Bioconversions of CO and H2/CO2 to acetic acid, ethanol and other products are well known. For example, in a recent book concise description of biochemical pathways and energetics of such bioconversions have been summarized by Das, A. and L. G. Ljungdahl, Electron Transport System in Acetogens and by Drake, H. L. and K. Kusel, Diverse Physiologic Potential of Acetogens, appearing respectively as Chapters 14 and 13 of Biochemistry and Physiology of Anaerobic Bacteria, L. G. Ljungdahl eds., Springer (2003). Any suitable microorganisms that have the ability to convert the syngas components: CO, H2, CO2 individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; and U.S. patent application Ser. No. 11/514,385 filed Aug. 31, 2006 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include *Clostridium Ljungdahli*, with strains having the identifying characteristics of ATCC 49587 (U.S. Pat. No. 5,173,429) and ATCC 55988 and 55989 (U.S. Pat. No. 6,136,577) and this will enable the production of ethanol as well as acetic acid and *Clostridium autoethanogenum* sp. nov., an anaerobic bacterium that produces ethanol from syngas. Jamal Abrini, Henry Naveau, Edmond-Jacques Nyns, Arch Microbiol., 1994, 345-351; Archives of Microbiology 1994, 161: 345-351. All of these references are incorporated herein in their entirety.

The microorganisms found suitable thus far for this invention require anaerobic growth conditions. Therefore the system will employ suitable control and sealing methods to limit the introduction of oxygen into the system. Since the microorganisms contact the liquid that circulates through the bioreactor system, a suitable redox potential will be maintained and monitored to insure anaerobic conditions. Anaerobic conditions in the liquid volume are usually defined as having a redox potential of less than −200 mV and preferably a redox potential in the range of from −300 to −500 mV. To further minimize exposure of the microorganisms to oxygen, the feed gas will preferably have an oxygen concentration of less than 1000 ppm, more preferably less than 100 ppm, and even more preferably less than 10 ppm.

The invention uses hydrophilic microporous membranes. At minimum the hydrophilic membrane must be operated at conditions such that there is restricted liquid permeability with respect to the biofilm. The restricted permeability prevents excessive fermentation liquid from migrating into the biofilm during normal operation of the system and interfering with contact between the gas and microorganisms.

The hydrophilic membrane must also have a surface for retaining the biofilm that restricts the penetration of the biofilm into the adjacent surface of the membrane. The surface of the membrane adjacent to the membrane thereby acts as a biofilm exclusion surface. Some minor penetration of the biofilm past the surface and into pores or surface irregularities of the membrane will occur but preferably such penetration of the biofilm is less than 10 μm, more preferably less than 5 μm and most preferably less than 2 μm. Some pores are necessary in the pore exclusion surface for the exchange of fermentation liquid between the membrane and the biofilm. Ways in which the pore exclusion surface may prevent the penetration of the biofilm are by pore size exclusion or by providing a high tortuosity factor for any pores in the biofilm exclusion surface.

Where the membrane use pore exclusion as the mean to inhibit migration to the biofilm past the surface upon which it form, the maximum pore size of the biofilm exclusion surface is typically no more than 0.5 μm. The biofilm exclusion surface may comprise a separate layer of the membrane that provides pores of the required diameter to inhibit the biofilm entry therein.

The biofilm exclusion surface may present pores greater than 0.5 μm and still inhibit the penetration of the biofilm past the adjacent surface if the pores at the surface of the biofilm have a high tortuosity factor. The tortuosity factor is described in many ways but for the purposes of this invention it is defined as the specific surface area S/V multiplied by the thickness of the exclusion layer L, where S is the total interior pore surface in the exclusion layer and V the volume of the layer. With this definition, the tortuosity is dimensionless. A membrane surface with a tortuosity of 10 or greater and an average interior pore size of no more than 10 μm will effectively inhibit the penetration of the biofilm . . . .

Hydrophilic, microporous membranes are widely available commercially, thus this invention requires little to no technology development with respect to the membrane itself. Most commonly the membranes take the form of hollow fibers or flat sheets. These membranes find extensive use for wastewater treatment. Membrane, membrane modules and cassettes are commercial products that could be adapted for use in this invention. Both ambient pressure or submerged membrane modules are commercially available as are pressure modules or cartridges.

The membranes are typically made of poly(vinylidene fluoride) (PVDF), polysulfone (PS), polyethersulfone (PES), polyethylene (PE), polypropylene (PP), poly(vinyl chloride) (PVC), or other polymeric materials. The pore size of the hydrophilic membrane is usually less than 0.5 μm, preferably less than 0.4 μm, more preferably less than 0.25 μm and most preferably in the ultrafiltration range of nominal MWCO of 10 to 500 kDa and more preferably in the range of 50 to 300 kDa. A typical pore size range is from 0.01 to 0.5 μm. The typical hollow fiber outer diameter is 0.4 to 2.8 mm and inner diameter 0.3 to 1.2 mm. For this invention, a pore size of 0.2 micron or less is desirable.

A hollow fiber membrane SteraporeSUN™, available from Mitsubishi Rayon (Tokyo, Japan), is made of PE with modified hydrophilic membrane surface. The hollow fiber has a nominal pore size of 0.4 μm and a fiber outer diameter of 0.54 mm. A SteraporeSUN™ membrane unit Model SUN21034LAN has a total membrane surface area of 210 m2, containing 70 membrane elements Model SUR334LA, each with 3 m2 membrane area.

The Microza® membranes from Asahi Kasei Chemicals (Tokyo, Japan) are hydrophilic hollow fiber membranes available in the ultrafiltration (MWCO 3,000 to 80,000) and microfiltration (0.1 to 0.25 μm) ranges. The Microza® ultrafiltration membranes have a "double skin" construction with a selective skin layer on both the inner and outer surface of the hollow fibers. Thus, the Microza® membranes, both the ultrafiltration and microfiltration types, can be used for both outside-in and inside-out filtration modes.

Another commercial hydrophilic hollow fiber membrane is the PVDF microfiltration membrane used for water filtration in the MEMCOR® CS submerged membrane systems from Siemens Water Technologies (Shrewsbury, Mass.). Another commercial hydrophilic hollow fiber membranes is the Zenon ZeeWeed® 500 membranes from GE Water & Process Technologies (Oakville, Ontario, Canada), which is a reinforced, composite membrane, comprising a porous woven inner support and a selective ultrafiltration layer made of PVDF coated on the outer surface of the support. Both the MEMCOR® CS membranes and the Zenon ZeeWeed® membranes are typically used in the outside-in filtration mode, rejecting microorganisms and other contaminants at the outer surface of the hollow fibers.

Hydrophilic hollow fiber membranes normally used in the inside-out mode for water filtration can be used for this invention, provided there is a biofilm exclusion zone near the outer surface to inhibit to penetration of the biofilm into the membrane by no more than 10 μm. Examples of such membranes include but are not limited to the ultrafiltration membranes from GE Healthcare and the HYDRAcap polyethersulfone ultrafiltration membranes from Hydranautics (Oceanside, Calif.). These membranes have the selective skin layer on the lumen surface but have finely porous structure in the membrane wall near the outer surface. Although pores greater than 0.5 μm exist on the outer surface, cells can be prevented from penetration deep into the membrane wall due to the tortuous path in the finely porous structure. It is also well know in the art that normally hydrophobic microporous membranes can be converted into hydrophilic membranes with surfactant treatment. U.S. Pat. No. 4,525,374 discloses a method to treat hydrophobic polypropylene or polytetrafluoroethylene membrane with a solution of triethanolamine dodecylbenzene sulfonate to render the membrane hydrophilic and is incorporated herein.

Membranes of the various geometries and compositions described above may be used in arrangements of unitary arrays or assemblies of varied composition in the process of this invention. Any suitable potting technique can be used to collect and provide the necessary assembly of individual membrane elements. In such membranes the gas and liquid can be brought into direct and intimate contact at the gas contact surface of the biofilm. Liquid is passed in the liquid side of the membranes via pumping, stirring or similar means to remove the liquid products such as ethanol and other soluble products formed; the products are recovered via a variety of suitable methods.

The syngas flows through the gas chamber or channels of the bioreactor system continuously or intermittently. The feed gas pressure is in the range of 1 to 1000 psig, preferably 5 to 400 psig, and most preferably 10 to 200 psig. Operating at higher gas pressures has the advantage of increasing the solubilities of gases in the liquid and the biofilm potentially increasing the rates of gas transfer and bioconversion. The differential pressure between the liquid and gas phases is managed in a manner that the membrane integrity is not compromised (e.g., the burst strength of the membrane is not exceeded) and the desired gas-liquid interface phase is maintained.

The reaction rate, gas concentration gradient and the thickness of the microorganisms can be maintained in equilibrium by control of the pressure differential across the membrane. Controlling the relative pressure on the liquid side of the membrane allows regulation of the and limiting of the fermentation broth across the membrane and into the biofilm. Such a limitation can affect the selectivity of the process for example the ensuring that sufficient dissolved CO penetrates into the entire biofilm will help achieve high selectivity for the production of ethanol versus acetate.

When the feed syngas contains moisture, condensation of water can occur at the microorganism/gas interface as consumption of syngas results in supersaturation of water. This condensed water leaves the biofilm/gas interface by dripping to the bottom of the bioreactor due to gravity.

Figure 1:
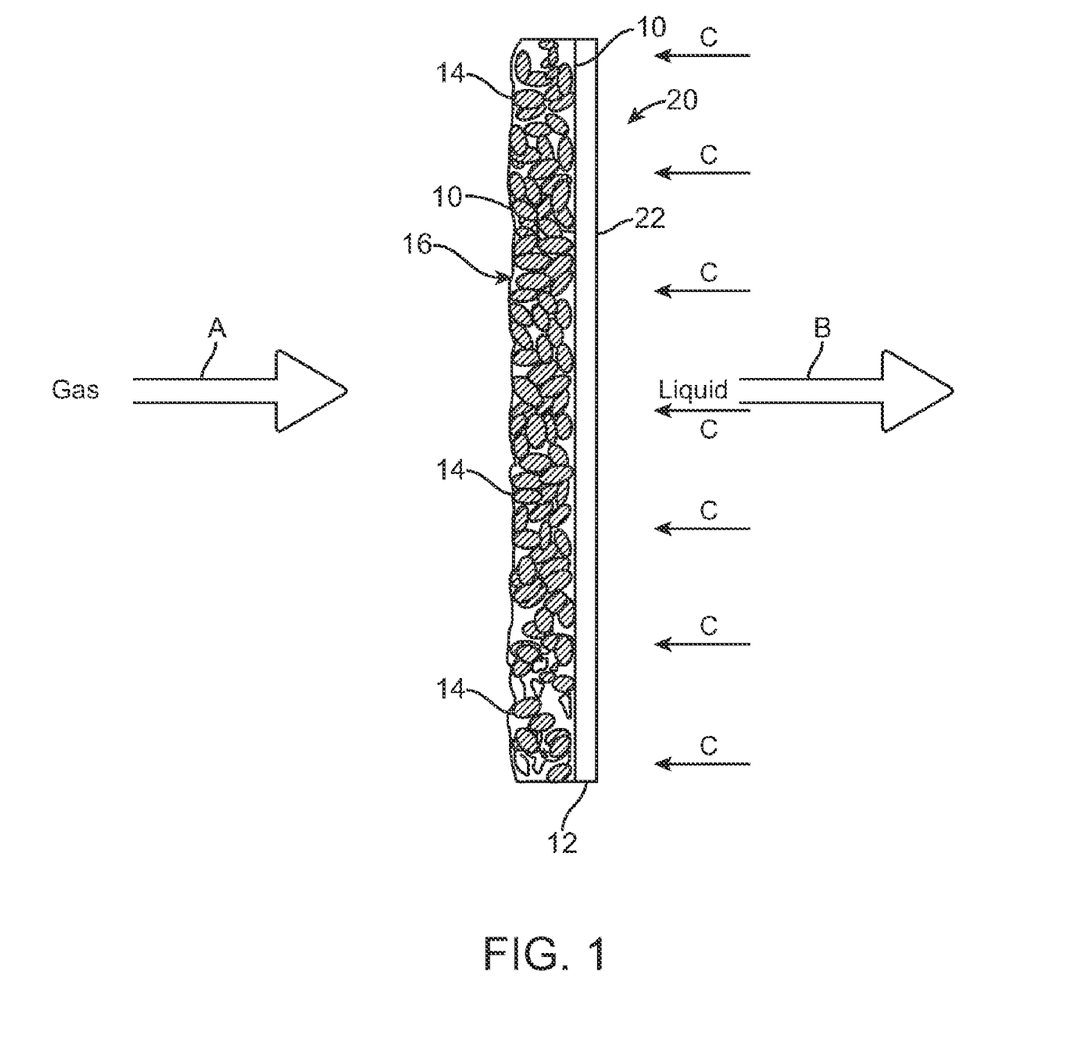
FIG. 1 is a schematic drawing showing a cross section of a hydrophilic membrane with a gas stream in contact with a biofilm that retains microorganisms thereon and an opposite side of the membrane in contact with fermentation liquid.

In this invention, a hydrophilic membrane arrangement, suitable for permeation of the fermentation liquid provides the separation between the liquid phase and feed gas comprising at least one of CO or a mixture of H2 and CO2 and a liquid phase. FIG. 1 shows more detail of the membrane configuration and interface in the operation of a representative bio-reactor system. FIG. 1 depicts a cross section of a single membrane element with a syngas stream A flowing to the gas contact side 10 of the hydrophilic membrane 12. The syngas components directly contact the microorganisms 14 retained as biofilm 16. The anaerobic acetogenic bacteria, *Clostridium ragsdalei*, having all of the identifying characteristics of ATCC No. BAA-622, is maintained in the biofilm and supplied with the fermentation liquid by permeation through the membrane 12. The fermentation liquid circulates on the opposite side of the membrane from the syngas side A and permeates through membrane 12 across a liquid contacting surface 22 transferring the fermentation liquid to the biofilm 16. The surface of gas contact side 10 that retains the microorganisms in biofilm 16 in contact with the gas stream provides equilibrium partitioning across the membrane 12 to keep the liquid and gas phases separated from each other. The pores that open to gas contact side 10 are much smaller than the width of the microorganisms retained in biofilm 16 so that contact side 10 occludes prevents the microorganisms from passing through membrane 12 and to liquid contacting surface 22. As a result the microorganisms 14 stay within biofilm 16 to gain metabolic energy by converting CO and H2/CO2 thereby growing and sustaining themselves within the biofilm 16.

The fermentation liquid flows back and forth across membrane 12. The hydrophilic membrane causes a portion of the liquid to flow toward the gas contact side 10 of the membrane and into biofilm 16 in the direction indicated by arrows C. Some circulation of liquid to the liquid phase side of the membrane occurs as indicated by the direction of arrow B and the fermentation liquid is withdrawn and separated to recover the desired products.

In one method of inoculating or seeding the membrane to form the biofilm, an aqueous solution containing microorganisms is introduced to the gas contacting side of the hydrophilic membrane, and then a slight trans-membrane pressure is applied to pass the solution through the membrane, creating a microorganism-free filtrate out of the liquid contact surface 22 and entrapping cells at the gas contact side surface. The microorganism-containing membrane is incubated for further microorganism growth and formation of the biofilm by supplying a syngas to the gas contact side and a liquid solution containing nutrients to the liquid contact side. During seeding, the seed solution containing microorganisms can either be static (dead end filtration) or circulated over the membranes (cross-flow filtration). Circulation of the seed solution can help achieve more uniform deposition of cells over the membrane surface.

Figure 2A:
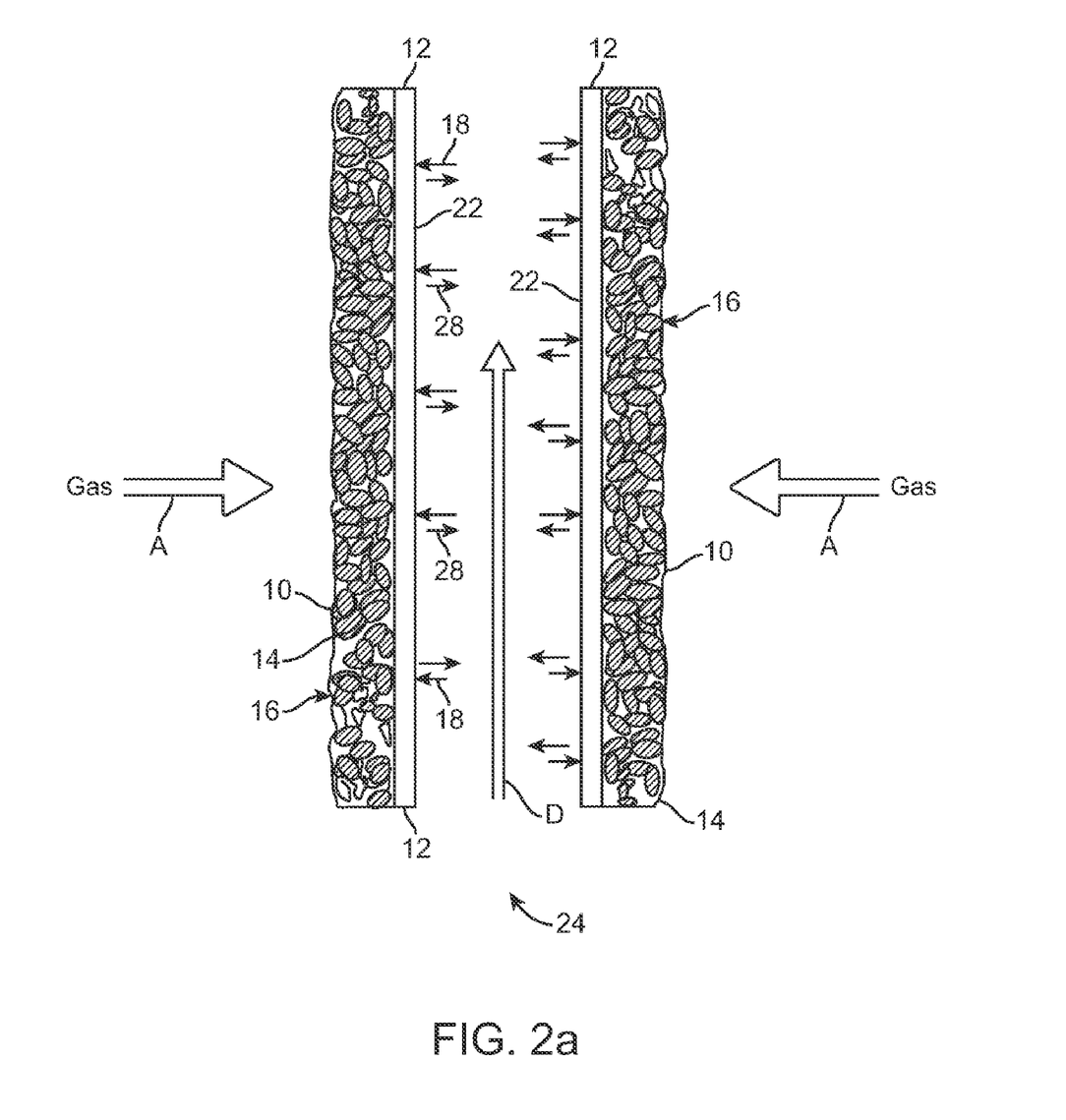
FIG. 2a is a schematic drawing showing a central passage formed by two membranes of the type shown in FIG. 1 with a gas stream contacting the outer wall and liquid contacting the inner walls.
Figure 2B:
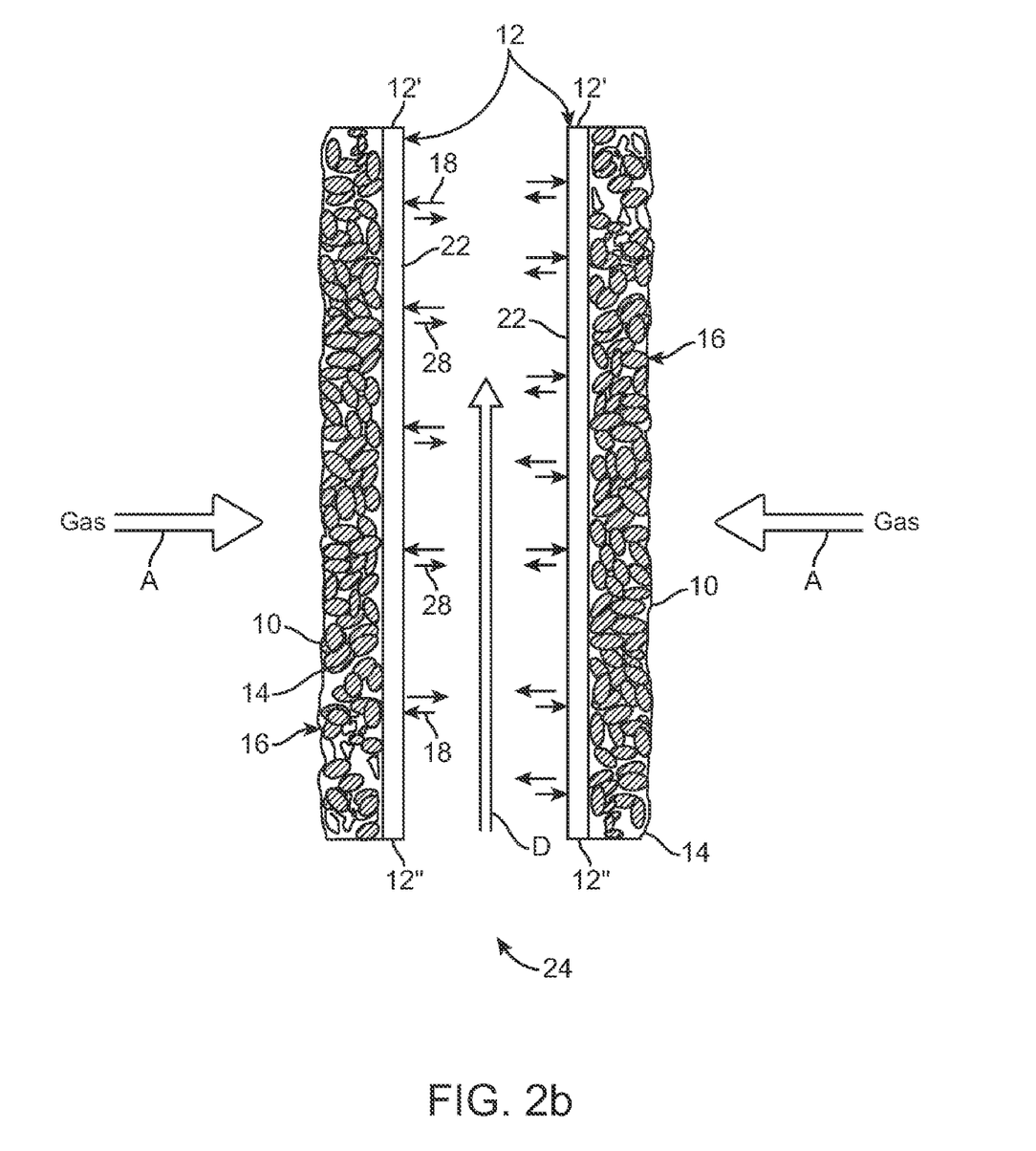
FIG. 2b is a schematic drawing showing a central passage formed by two membranes as in FIG. 2a by a membrane having two layers.

FIGS. 2a-b show various configurations of hydrophilic membranes with microorganisms present within a retained biofilm. In FIG. 2a two hydrophilic membrane portions 12 border a central liquid channel 24 through which a fermentation liquid circulates in the direction of stream D. The hydrophilic membranes on each side of liquid channel 24 functions in a similar manner to that described for the single membrane element of FIG. 1. A portion of the circulating fermentation liquid flows in the direction of arrows 18 across gas contact face 22 and into contact with the biofilm 16 to keep the microorganisms hydrated and supplied with nutrients. Syngas flows through the biofilm 16 and the microorganisms 14 to produce liquid products that flow into gas contacting side 10 carries out of the membrane 12 in the direction of arrows 28. The arrangement of FIG. 2a can use a flat sheet configuration or a tubular configuration and be particularly useful for good flow control and distribution on the liquid side In FIG. 2b the membrane 12 of FIG. 1 consists of a dual layer membrane. In FIG. 2b the gas contact face 22 is defined by a membrane layer 12" that retains the biofilm on one side. Another layer of the membrane 12' is contacted by the liquid stream that circulates in the direction of stream D. Layer 12' may comprise a support layer that retains layer 12" as a skin layer.

Figure 2C:
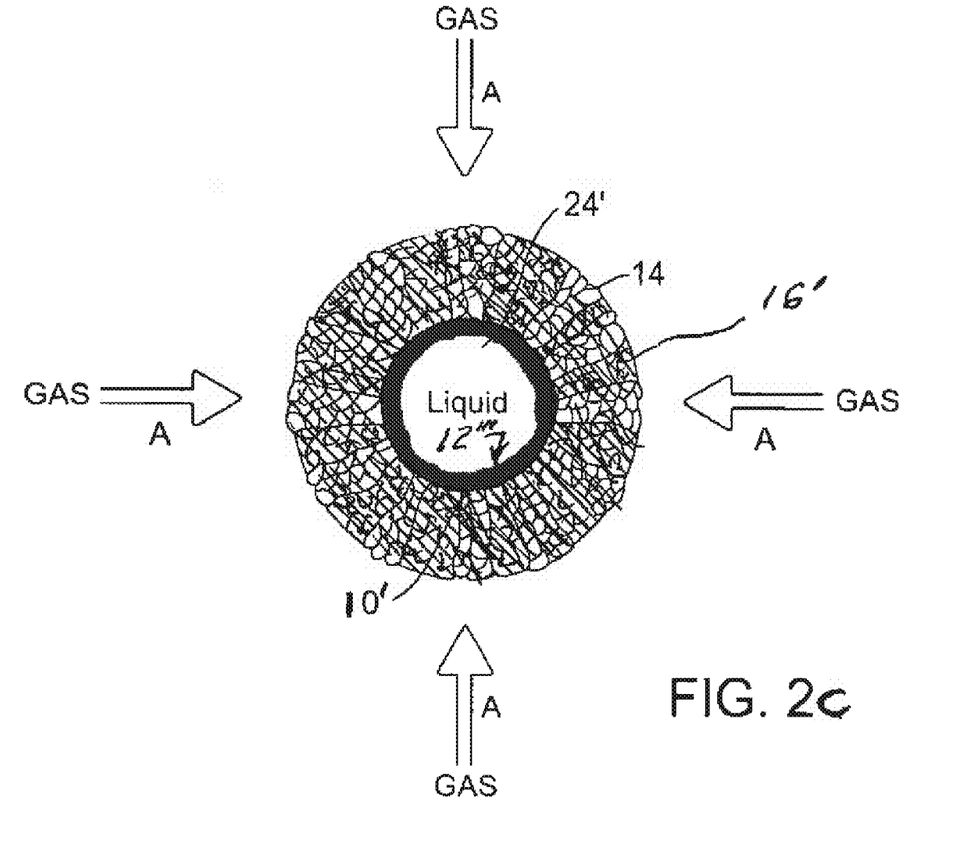
FIG. 2c is a schematic drawing showing a transverse cross-section of the asymmetric membrane of FIG. 1 made into a hollow fiber with the biofilm on the outside and the fermentation liquid flowing axially on the inside.

FIG. 2c shows a special case of FIG. 2a wherein the hydrophilic membrane 12''' wraps around in continuous form to provide a hollow fiber membrane with a central liquid channel 24'. In this case the syngas stream A flows radially inward into contact with the microorganisms 14 contained within an annular biofilm 16' on the gas contacting side 10 of the membrane. Fermentation liquid flows axially through liquid channel 24' and is recovered for separation and recovery of liquid products.

In most operations the membrane arrangements will benefit from occasional purging, scouring or flushing of the biofilm on the gas contacting surfaces. For this purpose, periodically during syngas fermentation, the liquid pressure can be increased for a short time to create a water flow through the membrane to purge some accumulated dead microorganisms or biopolymers out of the biofilm and from the gas contacting surface. This water is collected from the gas stream side of the bioreactor. Optionally this water stream may be treated for removal of suspended solids and recirculated to the bioreactor system.

Occasionally it is also desirable to clean the surface of the gas contacting side of the membrane by removal of the biofilm or other materials. One approach to this procedure begins with substantially removing the immobilized cells and the cleaning the membrane. To do this the gas supply is stopped, and the membrane is cleaned with cleaning solutions in manners similar to typical cleaning of microfiltration and ultrafiltration membranes. For example, the membrane is first soaked in a cleaning solution from both the sides, e.g. the biofilm side and the fermentation liquid side. The cleaning solution is formulated or selected to facilitate solubilization of microorganism and biopolymers. One of such solutions is an aqueous solution containing 2% NaCl and 0.4% NaOH, but many other formulations have been used for membrane cleaning, including some containing surfactants and hydrolytic enzymes. After soaking, the cleaning solution is circulated and a positive trans-membrane pressure is applied from the liquid contacting side to create a convective flow through the membrane and flush microorganism and biopolymers out of the gas contacting surface of the membrane. The soaking-filtration procedures can be repeated as needed, and different cleaning solutions can be used. After membrane cleaning, the membrane can be used for loading and growing new cells for syngas fermentation again.

Use of the hydrophilic membrane in the process of this invention allows simplification of the procedures for cleaning the surface of the membrane, removing debris and other material, and/or controlling the thickness of the biofilm. The gas distributing space outside the gas contacting side of the membrane may be flooded with a cleaning solution or any desired treating liquid. In most cases this amounts to filling a shell space that surrounds a plurality of hollow fiber membranes with liquid. Because the biofilm does not penetrate into the hydrophilic membrane the biofilm adheres much less to the gas contact side of the membrane and does not get trapped in the pores of the membrane leaving the biofilm more exposed and is easier to remove. This allows the use of milder chemical and physical conditions for membrane cleaning and helps maintain a long use life of the membrane. Thus the added solution may have enough solvent strength to remove the biofilm on its own. Agitating the liquid around the biofilm by sparging or dispersing a controlled amount of a gas stream into the liquid can serve to scour the biofilm to a desired degree further enhancing the ability to clean the gas contact face. It may also be possible to do a partial removal of the material in the biofilm by use of a gas stream to cause a reduction of the thickness of the biofilm without effecting its complete removal.

Any suitable gas stream can be used to sparge the liquid and create turbulence during the cleaning or biofilm removal step. The gas stream recovered from the bioreactor, i.e. tail gas, is highly suited for this purpose.

Figure 3:
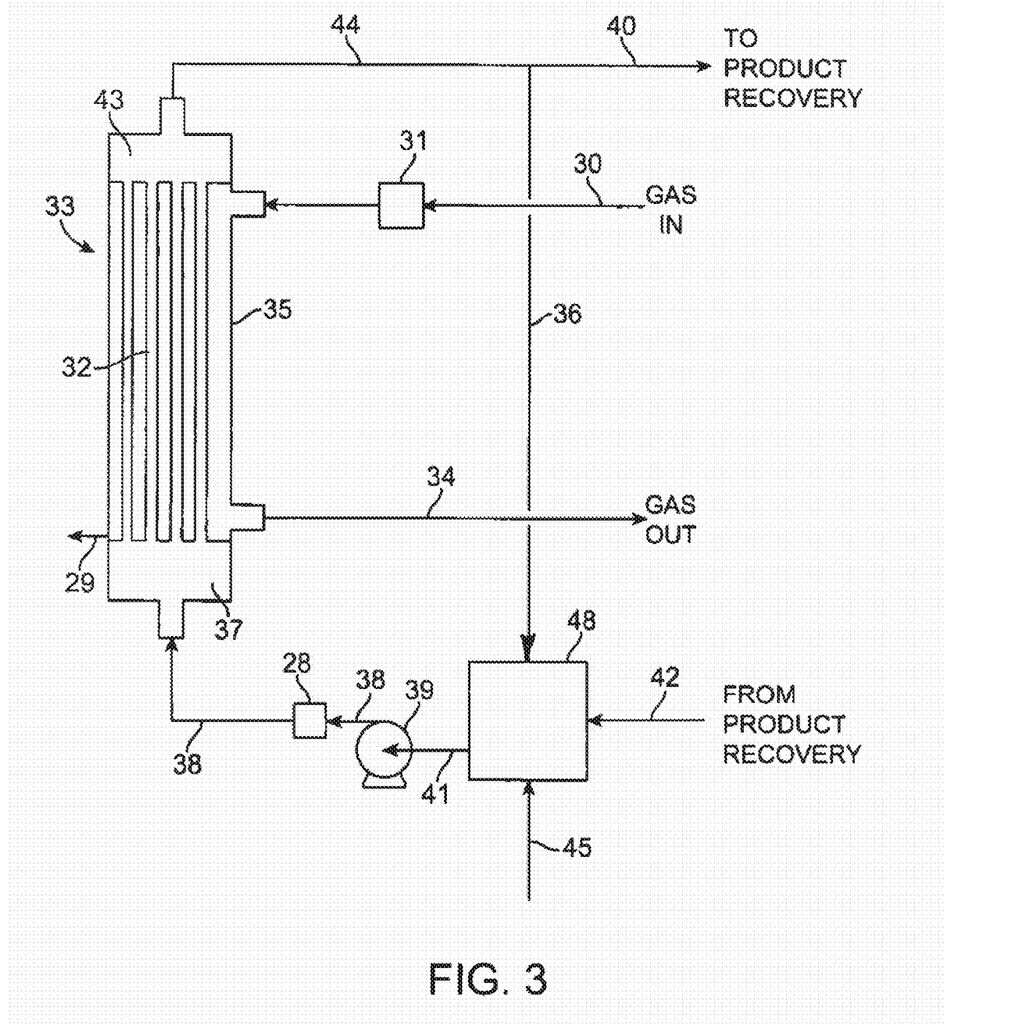
FIG. 3 is a schematic drawing of a bioreactor system showing gas and liquid circulation.

FIG. 3 illustrates a specific configuration of a bio-reactor system utilizing a membrane containing microorganisms. A gas supply conduit delivers a feed gas stream 30 containing syngas at a rate recorded by a flow meter 31 to a bioreactor 33. The bioreactor 33 includes a vessel 35 that surrounds the outside of the tubular or hollow fiber membrane elements 32. Membrane elements 32 contain microorganisms within a biofilm on the gas contacting side of the membrane.

A feed gas distribution chamber that surrounds the membrane elements 32 receives the feed gas stream and distributes it into direct contact with the outer surface of the membrane elements 32. The feed gas exits the vessel 35 via a line 34 such that a continuous addition of feed gas is established around the outer surface of membrane elements 32. The relative locations of the feed gas lines provide a downward direction of the bulk gas flow in the bioreactor 33.

Vessel 35 also contains a line 29 for draining liquid. Liquid may accumulate at the bottom of the vessel 35 for a variety of reasons as previously described such as condensation from moisture in the gas, flushing or purging of the membrane elements or periodic cleaning operations. Alternately line 34 may provide an outlet for liquid drainage. Liquid from condensation or flushing may be withdrawn from either location and treated for return to the fermentation liquid.

Fermentation liquid enters bioreactor 33 via a conduit 38 under pressure supplied by a pump 39 and at rate recorded by a flow meter 28. A chamber 37 distributes fermentation liquid to the tubular membranes 32 via the bottom ends of the lumens. At the top end of bioreactor 33 a chamber 43 collects the fermentation liquid from the top of the lumens for withdrawal of the liquid via a conduit 44. The relative locations of chambers 37 and 43 establish upward flow of the liquid through bioreactor 33 so that there is countercurrent flow with respect to the bulk gas flow and the liquid flow.

A line 40 withdraws a net portion of the liquid from line 44 while the remainder of the liquid returns to the bioreactor 33 via a recirculation line 36 and mixing chamber 48, a line 41 and line 38. Line 40 carries the liquid to product recovery facilities that recover liquid products. Depending on the nature of the desired product, there are a number of technologies that can be used for product recovery. For example, distillation, dephlegmation, pervaporation and liquid-liquid extraction can be used for the recovery of ethanol and n-butanol, whereas electrodialysis and ion-exchange can be used for the recovery of acetate, butyrate, and other ionic products. In all cases the product recovery step removes the desirable product from stream 40, while leaving substantial amounts of water and residual nutrients in the treated stream, part of which is returned to the bioreactor system via line 42 and mixing chamber 48.

Means for temperature and pH control for the liquid can be added anywhere along the re-circulating liquid loop, which consists of lines 38, 44, 36, and 41 as well as chambers 37, 43, and 48. A line 45 provides the nutrients needed to sustain the activity of the microorganisms to the re-circulating liquid loop chamber 48. Chamber 48 provides mixing of the nutrients and the other streams.

The flow rates of Streams 38 and 44, recirculated through the membrane unit, are selected so that there is no significant liquid boundary layer that impedes mass transfer near the liquid-facing side of the membrane. The linear velocity (define as total liquid flow rate divided by the total lumen cross sectional area of membrane elements 32) of the liquid tangential to the membrane should be in the range of 0.01 to 20 cm/s, preferably 0.05 to 5 cm/s, and most preferably 0.2 to 1.0 cm/s.

The membranes can be configured into typical modules as shown as an example in FIG. 3 for hollow fibers. The gas flows in the fine fibers that are bundled and potted inside a cylindrical shell or vessel through which the liquid is distributed and circulated. Very high surface areas in the range of 1000 m2 to 5000 m2 per m3 can be achieved in such modules.

During the bioconversion excess CO2 is generated and this gas can diffuse back and dilute out the concentrations of CO and H2 in the feed gas and thus reduce their mass transfer rates. Other types of membranes that preferentially permeate CO2 over CO and H2 can be used in the multi stage configuration as shown as an example in FIG. 4 where, using a membrane that selectively permeates CO2 and then returning the syngas enriched in CO and H2 to the bioreactor can be achieved.

Figure 4:
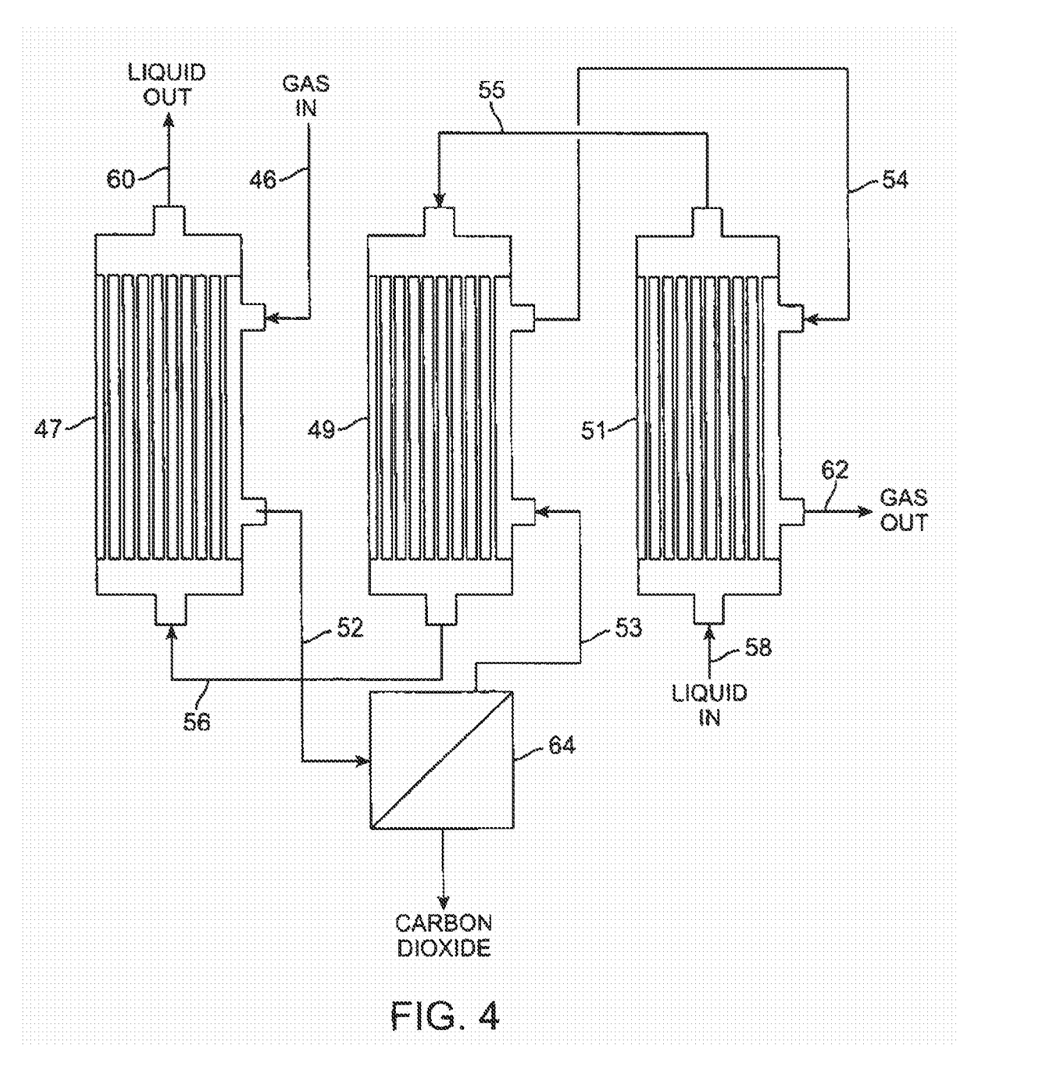
FIG. 4 is a schematic drawing showing a bioreactor system with multiple bioreactors arranged in series having intermediate carbon dioxide removal.

FIG. 4 depicts a system where the entering feed gas flows into bioreactor 47 via line 46 and serially through bioreactors 49 and 51 via lines 52, 53 and 54. At the same time liquid that contacts the microorganisms by permeating through the membrane enters the system via line 58 and flows countercurrently, with respect to the gas flow, through bioreactors 47, 49 and 51 via lines 55 and 56. Liquid products are recovered from the liquid flowing out of line 60 and a gas stream is withdrawn from the system via line 62. Separation unit 64 provides the stream of line 52 with intermediate removal of CO2 from the system via any suitable device or process such as a membrane or extraction step. Interconnecting lines 55 and 56 also provide the function of establishing continuous communication through all of the lumens of the different bioreactors so that any combined collection and distribution chambers provide a continuous flow path.

Example 1

An Xampler™ ultrafiltration membrane cartridge Model UFP-100-C-4X2MA from GE Healthcare is used as a membrane bioreactor for the conversion of carbon monoxide and hydrogen/CO2 into ethanol. This membrane cartridge contains hydrophilic hollow fibers with 1 mm inner diameter and rated at 100 kDa nominal MWCO. The active membrane surface area of the module is 0.085 m2 (based on lumen area). The temperature of the membrane cartridge is maintained at 37° C. with flexible heater attached around the cartridge and regulated with a temperature controller.

The membrane module is connected to a 7.5-liter BioFlo® 310 Fermentor from New Brunswick Scientific (Edison, N.J.). The fermentor contains 3 liters of the fermentation medium, which is agitated at 100 rpm and maintained at 37° C. and pH 5.9 with 1 N NaOH and 1 N HCl. The fermentation medium has the compositions shown in Tables 1&2. The medium is pumped from the fermentor, flows through the lumen side of the membrane module, and returns to the fermentor at a recirculation flow rate of 500 ml/min, unless otherwise stated. The fermentor is sparged with N2 at 100 std ml/min initially to maintain anaerobic conditions and switched to syngas overlay as described below.

Initially, the membrane cartridge is inoculated with 150 ml of an active culture of *Clostridium ragsdalei* ATCC No. BAA-622 by injecting the inoculum into the shell space. The inoculum solution is slightly pressurized to allow liquid to pass through the membrane into the lumen and retain the microbial cells on the outer surface of the membrane. Subsequently, a gas containing 40% CO, 30% H2, and 30% CO2 is fed to the shell side of the membrane cartridge at about 5 psig to displace the remaining inoculum liquid. The gas continues to be fed at 300 std ml/min throughout the remainder of the fermentation run and the residual gas from the module is directed to the fermentor headspace and exits the fermentor through a condenser and a vent filter. The gas pressure in the shell side of the membrane cartridge is maintained at about 1-5 psi greater than the liquid pressure in the lumen by adjusting a back-pressure valve downstream the gas outlet of the membrane cartridge.

The system is first operated in the batch mode for 2 days then switched to continuous operation, with continuous withdrawal of the fermentation liquid for product recovery and replenishing of fresh medium at 15 ml/hr. After 20 days of continuous operation, the withdrawn fermentation liquid contains 10 g/L ethanol and 2 g/L acetate.

TABLE 1

| Fermentation Medium Compositions | |
|---|---|
| Components | Amount per liter |
| Mineral solution, See Table 2(a) | 25 ml |
| Trace metal solution, See Table 2(b) | 10 ml |
| Vitamins solution, See Table 2(c) | 10 ml |
| Yeast Extract | 0.5 g |
| Adjust pH with NaOH | 6.1 |
| Reducing agent, See Table 2(d) | 2.5 ml |

TABLE 2(a)

| Mineral Solution | |
|---|---|
| Components | Concentration (g/L) |
| NaCl | 80 |
| NH$_4$Cl | 100 |
| KCl | 10 |
| KH$_2$PO$_4$ | 10 |
| MgSO$_4$•7H$_2$O | 20 |
| CaCl$_2$•2H$_2$O | 4 |

TABLE 2(b)

Trace Metals Solution

| Components | Concentration (g/L) |
|---|---|
| Nitrilotriacetic acid | 2.0 |
| Adjust the pH to 6.0 with KOH | |
| $MnSO_4 \cdot H_2O$ | 1.0 |
| $Fe(NH_4)_2(SO_4)_2 \cdot 6H_2O$ | 0.8 |
| $CoCl_2 \cdot 6H_2O$ | 0.2 |
| $ZnSO_4 \cdot 7H_2O$ | 1.0 |
| $NiCl_2 \cdot 6H_2O$ | 0.2 |
| $Na_2MoO_4 \cdot 2H_2O$ | 0.02 |
| $Na_2SeO_4$ | 0.1 |
| $Na_2WO_4$ | 0.2 |

TABLE 2(c)

Vitamin Solution

| Components | Concentration (mg/L) |
|---|---|
| Pyridoxine•HCl | 10 |
| Thiamine•HCl | 5 |
| Roboflavin | 5 |
| Calcium Pantothenate | 5 |
| Thioctic acid | 5 |
| p-Aminobenzoic acid | 5 |
| Nicotinic acid | 5 |
| Vitamin B12 | 5 |
| Mercaptoethanesulfonic acid | 5 |
| Biotin | 2 |
| Folic acid | 2 |

TABLE 2(d)

Reducing Agent

| Components | Concentration (g/L) |
|---|---|
| Cysteine (free base) | 40 |
| $Na_2S \cdot 9H_2O$ | 40 |

Example 2

A membrane module containing the hydrophilic PES HYDRAcap® ultrafiltration hollow fiber membranes from Hydranautics (Oceanside, Calif.) was used as a membrane bioreactor for the conversion of carbon monoxide and hydrogen into ethanol and acetate. The hollow fibers had 0.83 mm inner diameter and a permeability rated at 100 kDa nominal MWCO. The active membrane surface area of the module is 0.09 m2 based on the fiber outer diameter. The temperature of the membrane cartridge is maintained at 37° C. with flexible heater attached around the cartridge and regulated with a temperature controller.

The membrane module was connected to a 3.0-liter BioFlo® 110 Fermentor from New Brunswick Scientific (Edison, N.J.). The fermentor contained 1.5 liters of the fermentation medium, which was agitated at 50-100 rpm and maintained at 37° C. and pH 5.8 with 1 N NaOH and 1 N HCl. The fermentation medium had the compositions shown in Tables 3&4. The medium was pumped from the fermentor, flows through the lumen side of the membrane module, and returned to the fermentor at a recirculation flow rate of 100-200 ml/min, unless otherwise stated. The fermentor was sparged with N2 at 100 std ml/min initially to maintain anaerobic conditions and switched to syngas overlay as described below.

Initially, the membrane module was inoculated with 300 ml of an active culture of *Clostridium ragsdalei* ATCC No. BAA-622 by injecting the inoculum into the shell space. The inoculum was slightly pressurized to allow liquid volume to pass through the membrane into the lumen and the microbial cells to deposit on the exterior membrane surface. Subsequently, a gas containing 38% CO, 34% H2, 23.5% CO2 and 4.5% N2 was fed to the shell side of the membrane module at about 5 psig to displace the remaining inoculum liquid. The gas continued to be fed at 50 std ml/min initially and increased to 150 std ml/min later during the fermentation run and the residual gas from the module was directed to the fermentor headspace and exited the fermentor through a condenser and a vent filter. The gas pressure in the shell side of the membrane module is maintained at about 1-15 psi greater than the liquid pressure in the lumen by adjusting a back-pressure valve downstream the gas outlet of the membrane module.

Figure 5:
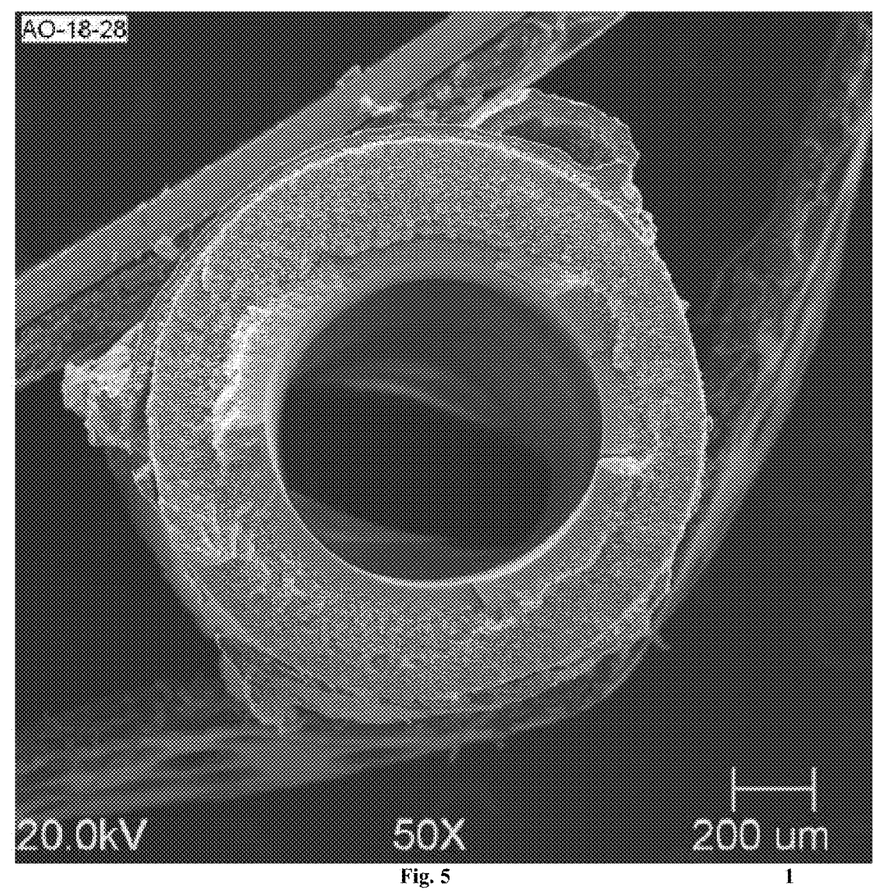
FIG. 5 is a Scanning Electron Micrograph of the Cross Section of a Hollow Fiber Used in Example 2, showing a 30-40 μm layer of biofilm on the exterior fiber surface.

The system was first operated in the batch mode for 3 days and then switched to continuous operation, with continuous withdrawal of the fermentation liquid for product recovery and replenish of fresh medium at 30 ml/hr. The fermentation liquid effluent contained 0.4 g/L ethanol and 4.2 g/L acetate at elapsed time of 193 hours and 0.0 g/L ethanol and 3.6 g/L acetate at 406 hours. The fermentation was terminated after 406 hours. The used hollow fibers were examined by using scanning electron microscopy, and a biofilm layer of 30-40 µm was found to be on the exterior surface of the fibers as shown in FIG. 5.

TABLE 3

Fermentation Medium Compositions

| Components | Amount per liter |
|---|---|
| Mineral solution, See Table 4(a) | 30 ml |
| Trace metal solution, See Table 4(b) | 10 ml |
| Vitamins solution, See Table 4(c) | 10 ml |
| Yeast Extract | 2.0 g |
| Adjust pH with NaOH | 6.1 |
| Reducing agent, See Table 4(d) | 5.0 ml |

TABLE 4(a)

Mineral Solution

| Components | Concentration (g/L) |
|---|---|
| NaCl | 40 |
| $NH_4Cl$ | 50 |
| KCl | 5 |
| $KH_2PO_4$ | 5 |
| $MgSO_4 \cdot 7H_2O$ | 10 |
| $CaCl_2 \cdot 2H_2O$ | 2 |

TABLE 4(b)

Trace Metals Solution

| Components | Concentration (g/L) |
|---|---|
| Nitrilotriacetic acid | 2.0 |
| Adjust the pH to 6.0 with KOH | |
| $MnSO_4 \cdot H_2O$ | 0.38 |
| $FeSO_4 \cdot 7H_2O$ | 3.66 |
| $CoCl_2 \cdot 6H_2O$ | 0.36 |
| $ZnSO_4 \cdot 7H_2O$ | 1.96 |
| $NiCl_2 \cdot 6H_2O$ | 0.078 |

TABLE 4(b)-continued

| | |
|---|---|
| $Na_2SeO_4$ | 0.34 |
| $Na_2WO_4 \cdot 2H_2O$ | 0.12 |

TABLE 4(c)

Vitamin Solution

| Components | Concentration (mg/L) |
|---|---|
| Pyridoxine•HCl | 10 |
| Thiamine•HCl | 5 |
| Roboflavin | 5 |
| Calcium Pantothenate | 5 |
| Thioctic acid | 5 |
| p-Aminobenzoic acid | 5 |
| Nicotinic acid | 5 |
| Vitamin B12 | 5 |
| Mercaptoethanesulfonic acid | 2 |
| Biotin | 2 |
| Folic acid | 2 |

TABLE 4(d)

Reducing Agent

| Components | Concentration (g/L) |
|---|---|
| Cysteine (free base) | 40 |
| $Na_2S \cdot 9H_2O$ | 40 |

The invention claimed is:

1. A process for converting a feed gas containing at least one of CO or a mixture of CO2 and H2 to a liquid product under anaerobic conditions and delivering the liquid product to a fermentation liquid, said process comprising:
   a) passing a feed gas into gas phase contact with a biofilm comprising immobilized microorganisms that produce liquid products from the feed gas;
   b) retaining the biofilm on a biofilm exclusion surface of a gas contacting side of a hydrophilic membrane wherein the biofilm exclusion surface is the outer surface of the gas contacting side and the biofilm exclusion surface inhibiting penetration of the biofilm into pores;
   b) passing a fermentation liquid comprising water and nutrients across a porous surface of a liquid contacting side of the membrane;
   c) permeating fermentation liquid from the liquid contacting side through the membrane and into contact with the biofilm;
   d) flowing fermentation liquid containing liquid products from the biofilm through the membrane and to the liquid contacting side of the membrane;
   (e) collecting fermentation liquid containing liquid products from the liquid contacting side of the membrane to recover liquid products from the process;
   wherein the feed gas is synthesis gas having an oxygen concentration of less than 1000 ppm, the liquid supply chamber retains a liquid having a redox potential in the range of less than −200 mV, the biofilm comprises microorganisms that produce ethanol and a liquid recovery chamber retains an ethanol containing liquid; and,
   wherein the feed gas passes serially through multiple assemblies of hollow fiber membranes, at least one feed gas chamber supplies feed gas for each hollow fiber membrane assembly and CO2 is removed from the gas as it passes between assemblies through the system.

2. The process of claim 1 wherein the biofilm exclusion surface has pores with effective diameters of no greater than 0.5 μm to inhibit penetration of the biofilm into the pores.

3. The process of claim 1 wherein the biofilm exclusion surface has pores with a sufficient tortuosity to inhibit penetration of the biofilm into the pores.

4. The process of claim 1 wherein the biofilm extends into the biofilm exclusion surface by no more than 10 μm.

5. The process of claim 1 wherein a feed gas chamber in fluid communication with the gas contacting side of the membrane supplies the feed gas to the membrane, a liquid supply chamber in fluid communication with the liquid contacting side of the membrane supplies fermentation liquid to the membrane, and a liquid recovery chamber in fluid communication with the liquid contacting side of the membrane recovers fermentation liquid containing liquid products.

6. The process of claim 1 wherein the hydrophilic membrane comprises a monolayer having a thickness of from 0.05 to 0.8 mm and an effective pore diameter of from 0.01 to 0.5 μm.

7. The process of claim 1 wherein the microorganism produces a liquid product comprising at least one of ethanol, n-butanol, hexanol, acetic acid, and butyric acid.

8. The process of claim 1 wherein the hydrophilic membrane comprises a plurality of hollow fiber membranes.

9. The process of claim 8 wherein the liquid product passes through the lumen of the hollow fiber membrane and the bulk feed gas flow through the assembly of hollow fiber membranes is countercurrent to the flow of fermentation liquid that flows in an axial direction through the lumens.

10. The process of claim 1 wherein the microorganisms in the bioreactor comprises a mono-culture or a co-culture of at least one of *Clostridium ragsdalei, Butyribacterium methylotrophicum, Clostridium ljungdahlii, Clostridium autoethanogenum, Clostridium woodii* and *Clostridium carboxydivorans*.

11. The process of claim 1 wherein the hydrophillic membrane comprises poly(vinylidene flouoride) (PVDF), polyethlylene (PE), polypropylene (PP), poly(vinyl chloride) (PVC) polysulfone (PS), polyethersulfone (PES).

12. The process of claim 1 wherein the hydrophilic membrane comprises a composite having a biofilm support layer and a liquid contacting layer of two different materials.

13. The process of claim 12 wherein biofilm exclusion surface comprises a skin having a thickness of no more than 5 μm on the outside of a membrane layer and the skin has a pore size of less than 0.5 μm.

14. The process of claim 1 wherein the gas contacting side of the hollow fiber membrane is temporarily flooded with liquid to remove at least a portion of the biolayer or material from the biolayer.

15. A process for converting a feed gas containing at least one of CO or a mixture of CO2 and H2 to a liquid product under anaerobic conditions and recovering the liquid product with the fermentation liquid, said process comprising:
   a) passing feed gas to a feed gas chamber for gas phase having fluid communication of the feed gas with a biofilm comprising immobilized microorganisms that produce liquid products from the feed gas;
   b) retaining the biofilm on a biofilm exclusion surface of a gas contacting side of a hydrophilic membrane having a hollow fiber form with a central lumen wherein the biofilm exclusion surface is the outer surface of the hollow fiber membrane and the biofilm exclusion surface inhibit penetration of the biofilm into the membrane by no more than 10~tm beyond the membrane surface;

c) passing a fermentation liquid comprising water and nutrients from a liquid supply chamber through the lumen and across a porous surface of the membrane;

d) permeating fermentation liquid from the lumen through the membrane wall and into contact with the biofilm;

e) permeating fermentation liquid containing liquid products from the biofilm through the membrane wall and into the lumen;

f) collecting fermentation liquid containing liquid products from the lumen in a liquid recovery chamber; and, g) passing fermentation liquid from the liquid recovery chamber to a product recovery section to recover liquid products from the process;

wherein the feed gas passes serially through multiple assemblies of hollow fiber membranes, at least one feed gas chamber supplies feed gas for each hollow fiber membrane assembly and $CO_2$ is removed from the feed gas as it passes from one assembly to the next through the system.

16. The process of claim 15 wherein the microorganisms in the bioreactor comprises a mono-culture or a co-culture of at least one of *Clostridium ragsdalei, Butyribacterium methylotrophicum, Clostridium ljungdahlii, Clostridium autoethanogenum, Clostridium woodii* and *Clostridium carboxydivorans* and produces a liquid product comprising at least one of ethanol, n-butanol, hexanol, acetic acid, and butyric acid.

17. The process of claim 15 wherein a continuous flow of feed gas having an oxygen concentration of less than 100 ppm passes across the gas contact side of the hydrophilic membrane.

18. The process of claim 15 wherein the hydrophillic membrane comprises poly(vinylidene flouoride) (PVDF), polyethlylene (PE), polypropylene (PP), poly(vinchloride) (PVC), polysulfone (PS) and polyethersulfone (PES).

19. The process of claim 15 wherein the feed gas chamber houses of the hollow fiber membrane and the feed gas chamber is occasionally flooded with liquid to remove at least a portion of the biofilm or material from the biolayer and while the chamber is flooded a gas stream is passed through the feed gas chamber along the membrane to sparge the biofilm and control its thickness.

20. A process for converting a feed gas containing at least one of CO or a mixture of $CO_2$ and $H_2$ to ethanol under anaerobic conditions and delivering the ethanol to a fermentation liquid, said process comprising:

a) passing feed gas to a feed gas chamber that houses a plurality of hollow fiber membranes and has fluid communication with a biofilm formed on the membranes comprising the microorganisms that produce ethanol from the feed gas wherein the outer surface of the membrane has pore size therein of 0.5~tm or less for inhibiting penetration of the biofilm into the pores of the membrane;

b) passing a fermentation liquid comprising water and nutrients from a liquid supply chamber through lumens of the membranes and across a porous surface of the membrane;

d) permeating fermentation liquid from the lumen through the membrane wall and into contact with the biofilm;

e) permeating fermentation liquid containing ethanol from the biofilm through the membrane wall and into the lumen; and, f) collecting fermentation liquid containing ethanol from the lumen in a liquid recovery chamber; and, g) passing fermentation liquid from the liquid recovery chamber to a product recovery section to recover ethanol from the process;

wherein the feed gas passes serially through multiple assemblies of hollow fiber membranes, at least one feed gas chamber supplies feed gas for each hollow fiber membrane assembly and $CO_2$ is removed from the feed gas as it passes from one assembly to the next through the system.

* * * * *